United States Patent
Kirby et al.

(12) 
(10) Patent No.: US 6,858,728 B2
(45) Date of Patent: Feb. 22, 2005

(54) METHOD FOR MAKING CAPROLACTAM FROM IMPURE ACN IN WHICH THA IS NOT REMOVED UNTIL AFTER CAPROLACTAM IS PRODUCED

(75) Inventors: Gregory S. Kirby, Avondale, PA (US); John J. Ostermaier, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 0 days.

(21) Appl. No.: 10/464,104

(22) Filed: Jun. 17, 2003

(65) Prior Publication Data
US 2004/0260087 A1 Dec. 23, 2004

(51) Int. Cl.⁷ ................... C07D 201/00; C07D 201/02
(52) U.S. Cl. ........................ 540/532; 540/539

(58) Field of Search .................. 540/532, 539

(56) References Cited

U.S. PATENT DOCUMENTS

| 2,301,964 A | 11/1942 | Martin et al. |
| 2,357,484 A | 9/1944 | Martin et al. |
| 6,069,246 A | 5/2000 | Chiarelli et al. |
| 6,169,199 B1 | 1/2001 | Rehfinger et al. |

FOREIGN PATENT DOCUMENTS

WO   WO 96/36601   * 11/1996

* cited by examiner

*Primary Examiner*—Bruck Kifle

(57) ABSTRACT

Method for making caprolactam from 6-aminocapronitrile that contains greater than 500 ppm tetrahydroazepine and its derivatives (THA) in which the THA is not removed from the method until after the caprolactam is produced.

2 Claims, 2 Drawing Sheets

METHOD FOR MAKING CAPROLACTAM FROM IMPURE ACN IN WHICH THA IS NOT REMOVED UNTIL AFTER CAPROLACTAM IS PRODUCED

BACKGROUND

U.S. Pat. No. 2,357,484, issued to Martin in 1944 discloses that epsilon-aminocapronitrile (ACN) can be converted into epsilon-caprolactam (CL) by contacting water with the ACN in the vapor phase in the presence of a dehydrating catalyst. Martin also described a liquid phase process to produce CL. See U.S. Pat. No. 2,301,964, issued Nov. 17, 1942.

In more recent years, technology has been developed to make inexpensive adiponitrile (ADN) by direct hydrocyanation of butadiene. This discovery has led to a renewed interest in the Martin CL process because the inexpensive ADN can be partially hydrogenated to produce an impure product that comprises ACN. This impure product also contains some byproducts of the hydrogenation reaction, notably tetrahydroazepine and its derivatives (both of which being referred to hereinafter as "THA").

Some recent patents have expressly taught that the THA and its derivatives must be removed from the impure ACN product before the ACN is converted into CL. See, for example, U.S. Pat. No. 6,169,199, issued Jan. 2, 2001.

Contrary to the suggestions in these patents, it has been found that the impure ACN that is recovered from the partial hydrogen of ADN—that contains greater than 500 ppm THA and its derivatives—can be processed in the vapor phase, as taught by Martin, to make CL without first removing the THA and its derivatives, and that the THA and its derivatives can be removed easily by distillation from the resulting crude CL product.

BRIEF DESCRIPTION OF THE DRAWING

The Drawing consists of two figures, FIG. 1 and FIG. 2, which are flow diagrams illustrating two alternative embodiments of the process of the present invention.

DETAILED DESCRIPTION OF THE INVENTION

As used throughout this application (unless the context suggests otherwise) the term "THA" is used to denote not only THA itself, but both THA and its derivatives. Such THA and its derivatives can be quantitatively measured by gas chromatography.

Figure 1:
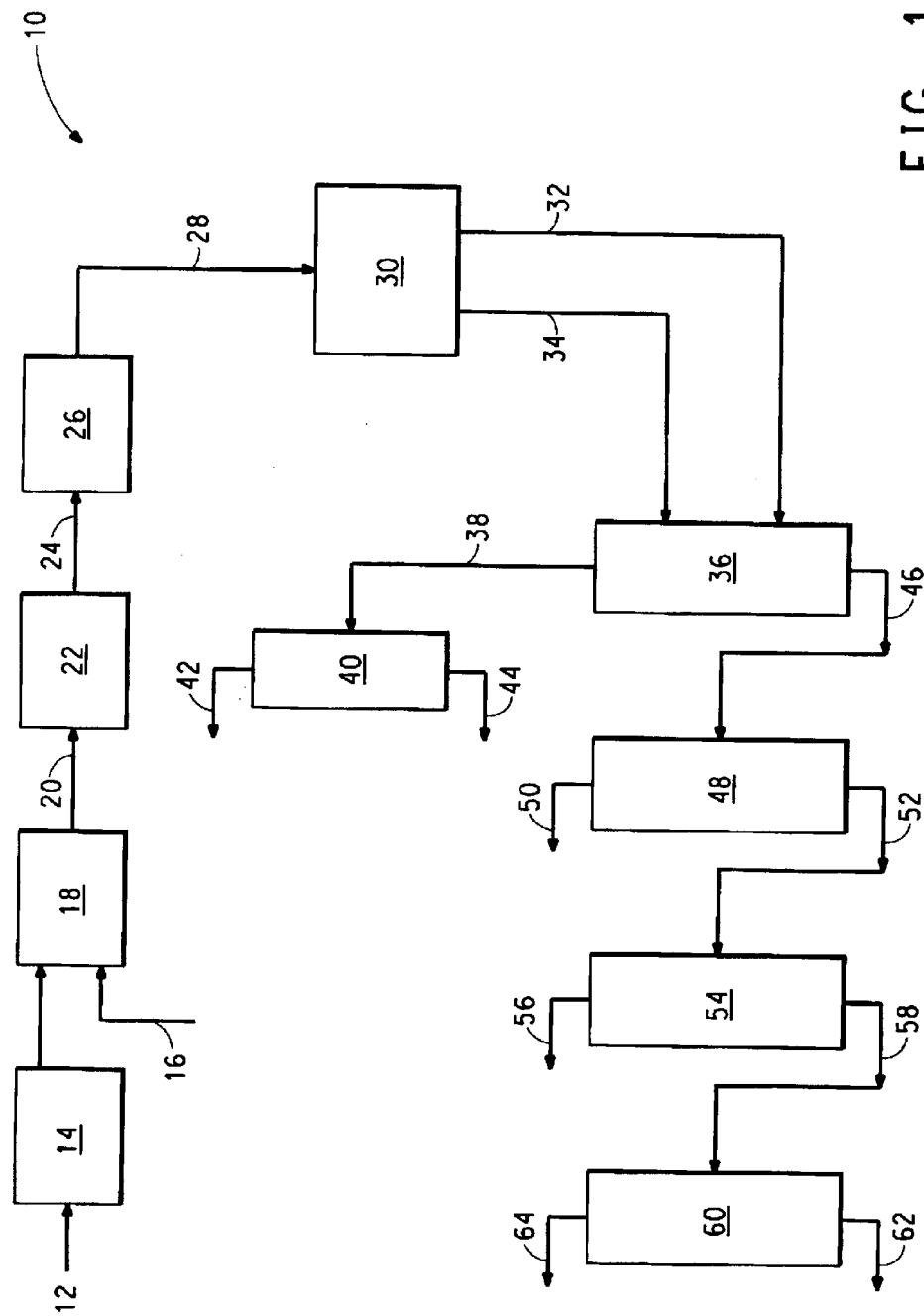

Referring now to FIG. 1, there is shown in schematic form apparatus 10 for practicing the first embodiment of the current invention. An impure ACN feed material 12 that can contain greater than 500 ppm THA is fed by a pump (not shown) into a heat exchanger 14 which heats the incoming impure ACN to a temperature of about 235 deg C. The heated, impure ACN is mixed with steam 16 in a vaporizer 18. A vapor phase mixture 20 of ACN, THA and water leaves the vaporizer 18 and is fed into at least one super heater 22 that heats the vapor 20 to a temperature of 275 deg C. A superheated vapor 24 exits the super heater and is fed into a CL synthesis reactor 26. The reactor 26 contains a dehydrating catalyst, as taught by Martin, such as activated alumina, titanium dioxide, vanadium oxide, etc. The reactor can be a fixed bed or a fluidized bed reactor.

The heat of reaction is removed from the reactor by a heat transfer fluid (not shown) that controls the reaction temperature within a range of 300 to 325 deg C. A suitable heat transfer fluid is the material sold by DOW Chemical Company under the trademark "Dowtherm-A." The reaction occurring inside reactor 26 produces CL and ammonia. Conducting the reaction in the vapor phase prevents the formation of CL oligomers. A major portion of the THA present in the superheated vapor 24 passes through the reactor 26 without chemical transformation.

Exiting the reactor 26 is a vaporous product stream 28 that comprises CL, ammonia, water, unreacted ACN and unreacted THA. The product stream 28 is fed into a partial condenser 30 that condenses some of the water, and a major portion of each of the CL, the unreacted ACN and unreacted THA to produce a liquid stream 32. Also exiting the condenser 30 is a vapor stream 34 that comprises some water vapor, ammonia gas and perhaps a minor amount of THA, ACN, and CL. Both the stream 32 and the stream 34 are fed into different stages of an ammonia removal distillation column 36. Stream 32 is fed to the lower part of column 36, while stream 34 is fed to a higher stage than that to which stream 32 is fed. Column 36 operates slightly above atmospheric pressure and removes essentially all of the ammonia as distillate 38 along with most of the water. Distillate 38 is fed into a high pressure ammonia refining column 40 from which anhydrous ammonia product is removed as distillate 42 and water (together with trace amounts of organic materials) is removed as a bottoms 44. The exact pressure is not critical, but will depend upon the temperature of available heat removal fluids (not shown). Column 36 produces a bottoms 46 that comprises some water, unreacted ACN, unreacted THA, CL, and some high boilers. Column 36 can contain trays or packing (not shown), and preferably is operated with a bottoms temperature below about 160 deg C. to avoid the formation of CL oligomers. The bottoms 46 is fed into a vacuum dehydration column 48 that contains structured packing (not shown). Liquid water is removed from column 48 as distillate 50. A bottoms 52 is removed from column 48. The bottoms 52 comprises CL, unreacted ACN, most of the unreacted THA and some high boilers. Preferably, column 48 is operated with a bottoms temperature below about 160 deg C. to avoid the formation of CL oligomers. The bottoms 52 is fed into a vacuum low boiler removal column 54, again operating with a bottoms temperature below about 160 deg C. Column 54 contains structured packing (not shown). A distillate 56 is removed from column 54. The distillate 56 comprises unreacted ACN, some CL, most of the unreacted THA and some water. A bottoms 58 is removed from column 54. The bottoms comprises CL and high boilers. The bottoms 58 is fed into a vacuum high boiler removal column 60, containing structured packing (not shown) and operating with a bottoms temperature below about 160 deg C. High boilers and a minor portion of the incoming CL are removed as bottoms 62. The majority of the incoming CL is removed as distillate 64. This CL is the desired product of the process of the current invention. This CL is suitable for polymerization to make Nylon 6 polymer. If desired, the bottoms 62 can be fed to a wiped film evaporator (not shown) to recover CL that is present in the bottoms 62. This recovered CL can be fed to high boiler removal column 60.

If the present process is operated on a commercial scale, a substantial amount of water will result in streams 44 and 50. To increase the economic efficiency of the process, these streams may be combined, appropriately treated, and recycled back to the reactor 26.

Figure 2:
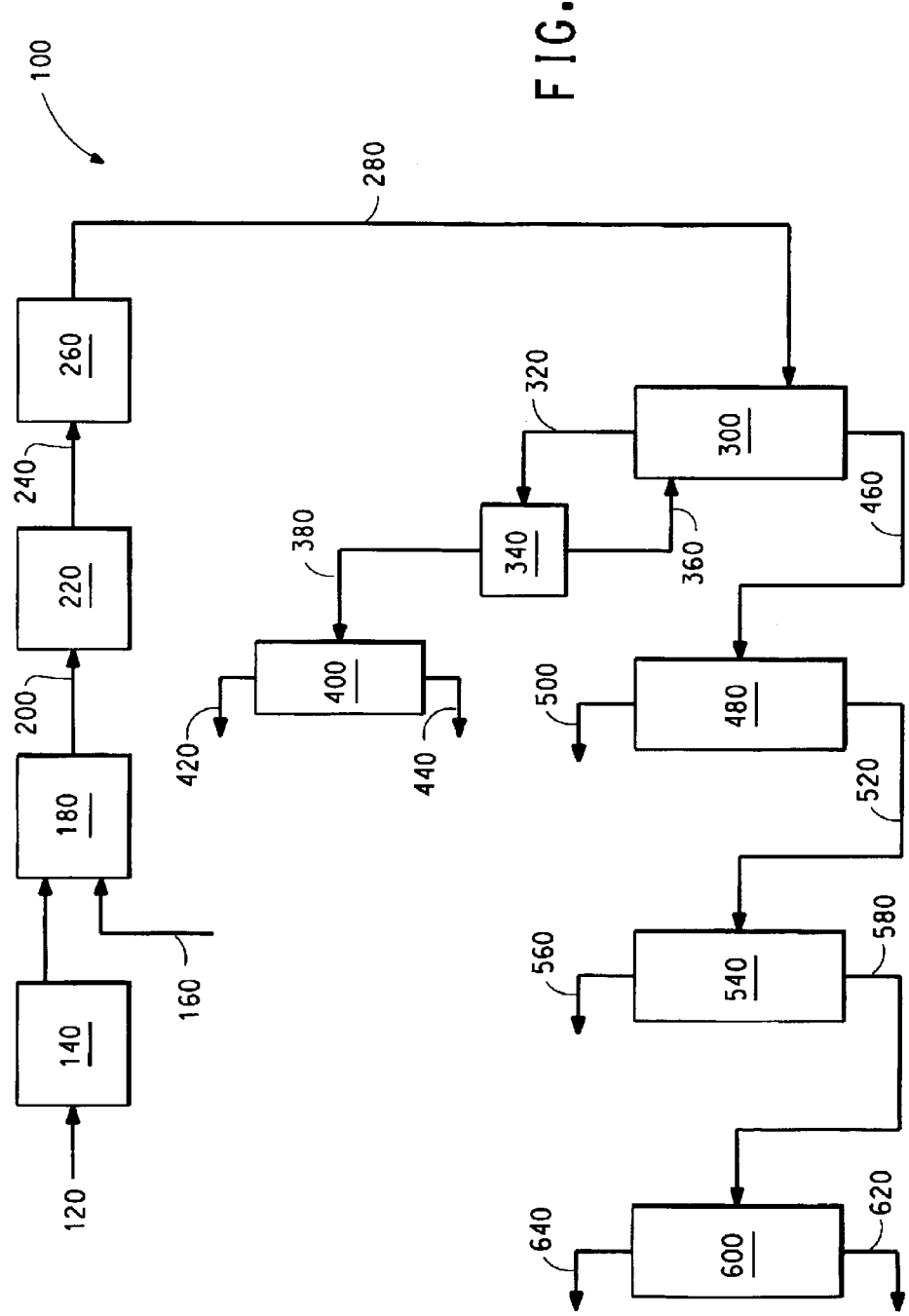

Referring now to FIG. 2, there is shown in schematic form apparatus 100 for practicing a second embodiment of the current invention. An impure ACN feed material 120 that can contain greater than 500 ppm THA is fed by a pump (not shown) into a heat exchanger 140 which heats the incoming impure ACN to a temperature of about 235 deg C. The heated, impure ACN is mixed with steam 160 in a vaporizer 180. A vapor phase mixture 200 of ACN, THA and water leaves the vaporizer 180 and is fed into at least one super heater 220 that heats the vapor 200 to a temperature of 275 deg C. A superheated vapor 240 exits the super heater and is fed into a CL synthesis reactor 260. The reactor 260 contains a dehydrating catalyst, as taught by Martin, such as activated alumina, titanium dioxide, vanadium oxide, etc. The reactor can be a fixed bed or a fluidized bed reactor.

The heat of reaction is removed from the reactor by a heat transfer fluid (not shown) that controls the reaction temperature within a range of 300 to 325 deg C. A suitable heat transfer fluid is the material sold by DOW Chemical Company under the trademark "Dowtherm-A." The reaction occurring inside reactor 260 produces CL and ammonia. Conducting the reaction in the vapor phase prevents the formation of CL oligomers. A major portion of the THA present in the superheated vapor 240 passes through the reactor 260 without chemical transformation.

Exiting the reactor 260 is a vaporous product stream 280 that comprises CL, ammonia, water, unreacted ACN and unreacted THA. In contrast to the first embodiment, the product stream 280 is fed directly, without condensing, to the lower part of an ammonia removal distillation column 300. This reflects a difference from the teachings of U.S. Pat. No. 6,069,246, issued May 30, 2000, wherein crude CL produced from the vapor phase cyclizing hydrolysis of ACN is cooled, over a period of less than or equal to 1 hour, to a temperature below or equal to 150 deg C., before it is distilled, to limit the formation of oligomers. Since it is well known by those skilled in the art that oligomerization does not readily occur in the vapor phase and is normally confined to the liquid phase, an alternative means of limiting oligomer formation, as practiced in this second embodiment, is to feed the vapor stream 280 leaving the hydrolysis reactor 260 as vapor to the CL distillation train, at a temperature much higher than 150 deg C., either directly or after some cooling. This has the added benefit of directly utilizing the heat content of the vapor phase reaction product in the subsequent distillation, without the inefficiencies of indirect heat recovery by heat exchange with other process streams, utility streams, or other heat-exchange fluids. Column 300 operates slightly above atmospheric pressure and removes essentially all of the ammonia and most of the water in an overhead stream 320. Column 300 is equipped with a condenser 340 having sufficient capacity to condense overhead stream 320 to produce a liquid reflux stream 360, a liquid distillate stream 380 and a minor non-condensable vapor vent stream (not shown). Alternatively, vaporous product stream 280 can be passed through a cooler (not shown) to cool the vapor, but not to a temperature below its dew point, as a means of reducing the requirements on condenser 340 while still limiting the formation of oligomers. The cooling medium for said cooler can be, but is not limited to, circulating cooling water, air, other process streams, or other heat-exchange fluids. Distillate 380 is fed into a high pressure ammonia refining column 400 from which anhydrous ammonia product is removed as distillate 420 and water (together with trace amounts of organic materials) is removed as a bottoms 440. The exact pressure is not critical, but will depend upon the temperature of available heat removal fluids (not shown). Column 300 produces a bottoms 460 that comprises some water, unreacted ACN, unreacted THA, CL, and some high boilers. Column 300 can contain trays or packing (not shown), and preferably is operated with a bottoms temperature below about 160 deg C. to avoid the formation of CL oligomers. The bottoms 460 is fed into a vacuum dehydration column 480 that contains structured packing (not shown). Liquid water is removed from column 480 as distillate 500. A bottoms 520 is removed from column 480. The bottoms 520 comprises CL, unreacted ACN, most of the unreacted THA and some high boilers. Preferably, column 480 is operated with a bottoms temperature below about 160 deg C. to avoid the formation of CL oligomers. The bottoms 520 is fed into a vacuum low boiler removal column 540, again operating with a bottoms temperature below about 160 deg C. Column 540 contains structured packing (not shown). A distillate 560 is removed from column 540. The distillate 560 comprises unreacted ACN, some CL, most of the unreacted THA and some water. A bottoms 580 is removed from column 540. The bottoms comprises CL and high boilers. The bottoms 580 is fed into a vacuum high boiler removal column 600, containing structured packing (not shown) and operating with a bottoms temperature below about 160 deg C. High boilers and a minor portion of the incoming CL are removed as bottoms 620. The majority of the incoming CL is removed as distillate 640. This CL is the desired product of the process of the current invention. This CL is suitable for polymerization to make Nylon 6 polymer. If desired, the bottoms 620 can be fed to a wiped film evaporator (not shown) to recover CL that is present in the bottoms 620. This recovered CL can be fed to high boiler removal column 600.

If the present process is operated on a commercial scale, a substantial amount of water will result in streams 440 and 500. To increase the economic efficiency of the process, these streams may be combined, appropriately treated, and recycled back to the reactor 260.

EXAMPLE

This example illustrates the first embodiment of the process of the present invention.

A solution containing approximately 50% by wt. ACN and 50% by wt. water was vaporized, and then reacted over a dehydration (alumina) catalyst at 300 deg C. and atmospheric pressure in the vapor phase. The amount of THA present in the ACN used to make the solution was 1800 ppm, as determined by gas chromatographic analysis. The organic product exiting the reactor contained 1.25% by wt. unreacted ACN, 700 ppm THA, and the balance substantially caprolactam, on an anhydrous basis. Some other trace impurities were also present, as well as a stoichiometric amount of ammonia reaction product and unconverted water. This data indicates some consumption of THA in the reaction step to form unidentified products. The vapor phase product was then cooled to produce an aqueous caprolactam solution that was saturated with ammonia.

The aqueous caprolactam solution was flashed at atmospheric pressure and 145 deg C. in a single stage still to remove the ammonia and the majority of the water. The remaining material was again flashed in a single stage still at 120 torr (16 kPa) pressure and 145 deg C. to remove additional water.

Next, 1.4 liters of molten caprolactam were then transferred to a batch still which contained 4.5 feet of Sulzer BX® mesh packing. The still was operated at a head pressure of 10 torr (1.3 kPa). The ACN and THA were then distilled overhead at a reflux ratio of 50 to 1. Four successive 50 ml distillation cuts were taken overhead to remove the THA and ACN. Gas chromatographic analysis of the distillate cuts are as follows:

| Component | Cut #1 | Cut #2 | Cut #3 | Cut #4 |
|---|---|---|---|---|
| THA (% by wt) | 0.758 | 0.066 | 0.022 | 0.014 |
| ACN (% by wt) | 45.3 | 4.46 | 0.492 | 0.187 |

These data indicate that both the THA and ACN are successfully being removed from the caprolactam by distillation.

After Cut #4 above was taken, the reflux ratio was reduced to 1 to 1, and the product caprolactam was distilled overhead. A total of 850 ml of refined caprolactam product was recovered, which contained no detectable amounts by gas chromatography of THA or ACN. High boilers present in the initial material charged to the batch still remained in the pot residue.

This example illustrates that THA can be readily removed from caprolactam by distillation. This example demonstrates that it is possible to utilize ACN containing levels of THA greater than 500 ppm for caprolactam synthesis and remove the residual THA from the caprolactam product.

This example, while performed in a batch mode, illustrates that the desired separations can also be carried out in a series of continuous columns, where an improved recovery of caprolactam would be expected.

What is claimed is:

1. A method for making caprolactam from an impure 6-aminocapronitrile (ACN) obtained by the partial hydrogenation of adiponitrile, said impure 6-aminocapronitrile comprising both ACN and a minimum of 500 ppm tetrahydroazepine and its derivatives (THA), comprising the steps of:

(1) contacting the impure ACN comprising both ACN and THA with water at elevated temperature in the presence of a dehydration catalyst, both the impure ACN and the water being in the vapor phase, to produce a vapor phase reaction product that comprises caprolactam (CL), ammonia, water, ACN, and THA;

(2) separating the ammonia and a major portion of the water from the vapor phase reaction product to produce a solution comprising caprolactam and a minor portion of the water, and then separating the water from the solution to produce a melt comprising caprolactam, ACN and THA;

(3) introducing the melt into a low boiler removal distillation column and removing a major portion of both the THA and ACN as a distillate, and removing caprolactam, high boilers and at most a minor portion of both the THA and ACN as a bottoms; and (4) introducing the bottoms into a high boiler removal distillation column and removing caprolactam and at most a minor portion of the high boilers as a distillate product and removing a major portion of the high boilers as a bottoms.

2. The method of claim 1 wherein in step (2) the ammonia and the major portion of the water are separated from the vapor phase reaction product by partially condensing the vapor phase reaction product to produce a vapor stream that comprises ammonia and water, and a liquefied stream that comprises water, CL, unreacted ACN, and THA, introducing the vapor stream into a predetermined stage of a distillation column and introducing the liquid stream into a stage of the distillation column lower than the predetermined stage, and withdrawing as a bottoms the solution comprising CL and a minor portion of the water.

* * * * *